United States Patent [19]

Daniell et al.

[11] Patent Number: 5,558,084

[45] Date of Patent: Sep. 24, 1996

[54] HUMIDIFIER WITH DELIVERY TUBE CONDENSATION PREVENTING STRUCTURE AND CONTROL

[75] Inventors: Michael G. Daniell; Andrew B. Clark, both of Auckland, New Zealand

[73] Assignee: Fisher & Paykel Limited, Auckland, New Zealand

[21] Appl. No.: 955,503

[22] Filed: Oct. 2, 1992

[30] Foreign Application Priority Data

Oct. 4, 1991 [NZ] New Zealand ............................ 240102

[51] Int. Cl.$^6$ ............................ A61M 16/16; H05B 3/00; F24F 6/02

[52] U.S. Cl. ............................ 128/203.17; 128/203.12; 128/204.17; 261/DIG. 34; 261/130; 261/142; 165/222

[58] Field of Search ........................ 128/203.12, 203.16, 128/203.17, 203.26, 203.27, 204.14, 201.13, 204.17; 62/248; 236/44 C, 44 R, 91 F, 91 G, DIG. 13, 44 A, 99 C, 78 B; 261/129, 130, 131, 137, 138, 139, DIG. 27, DIG. 32, DIG. 34, 142, DIG. 65; 165/17, 19–21, 921

[56] References Cited

U.S. PATENT DOCUMENTS

| | | | |
|---|---|---|---|
| 2,712,927 | 7/1955 | Blum | 261/129 |
| 2,953,355 | 9/1960 | Hungate | 261/130 |
| 3,659,604 | 5/1972 | Melville et al. | 128/212 |
| 3,869,529 | 3/1975 | Follette | 261/130 |
| 3,903,883 | 9/1975 | Pecina et al. | 128/200.21 |
| 3,987,133 | 10/1976 | Andra | 261/130 |
| 4,060,576 | 11/1977 | Grant | 261/130 |
| 4,110,419 | 8/1978 | Miller | 261/142 |
| 4,201,204 | 5/1980 | Rinne et al. | 261/130 |
| 4,322,594 | 3/1982 | Brisson | 219/497 |
| 4,346,048 | 8/1982 | Gates | 261/130 |
| 4,389,353 | 6/1983 | Gates | 261/130 |
| 4,448,035 | 5/1984 | Moriyama et al. | 128/203.16 |
| 4,590,772 | 5/1986 | Nose et al. | 128/203.16 |
| 4,595,139 | 6/1986 | Levine | 128/203.16 |
| 4,621,632 | 11/1986 | Bartels et al. | 128/203.17 |
| 5,163,423 | 11/1992 | Suzuki | 128/205.23 |
| 5,240,177 | 8/1993 | Muramatsu et al. | 128/203.16 |

FOREIGN PATENT DOCUMENTS

| | | |
|---|---|---|
| 2630917 | 11/1989 | France. |
| 1294808 | 11/1972 | United Kingdom ............... 128/203.17 |
| 2097272 | 11/1982 | United Kingdom. |

*Primary Examiner*—Kimberly L. Asher
*Attorney, Agent, or Firm*—Trexler, Bushnell, Giangiorgi & Blackstone, Ltd.

[57] ABSTRACT

A humidifier having an ambient temperature sensor for sensing the temperature of the ambient air in the environment in which the humidifier is located. A difference temperature selector is provided to allow a user to select a difference temperature which is the difference in temperature between the sensed ambient temperature and a comfortable and efficient temperature for supply of the humidified gases provided by the humidifier to a patient or user. The humidifier controls the temperature of the humidified gases it provides to the patient to the selected difference temperature above the sensed ambient temperature, so that any change in the sensed ambient temperature results in a corresponding change in the temperature of humidified gases supplied to the patient or user. This construction prevents or minimises the condensation which occurs at low ambient temperatures in the gases supply conduit provided between the humidifier and the patient or user.

7 Claims, 3 Drawing Sheets

HUMIDIFIER WITH DELIVERY TUBE CONDENSATION PREVENTING STRUCTURE AND CONTROL

BACKGROUND OF THE INVENTION (1) Field of the Invention

This invention relates to humidifiers of the type for use in providing humidified gases to a user such as a patient requiring humidified gases. The humidifier of this invention may be used in a hospital environment but has been devised particularly for use in a home care environment.

(2) Description of the Prior Art

Humidifiers in which gases to be breathed by a patient are humidified by being passed over a heated water bath are known. Generally in this type of humidifier, particularly when used in a hospital environment, gases are regulated to a fixed, preset temperature for supply to the patient, or the water bath temperature is regulated, or an open loop controller may regulate power to the water bath. In a hospital environment, where the ambient temperature of the atmosphere within the hospital is controlled by air conditioning for example, the required temperature for the humidified gases supplied by the apparatus may be controlled within set temperature parameters. The controlled temperature parameters ensure that the humidified gases are sufficiently close to the ambient temperature to prevent condensation within the breathing conduit which supplies humidified gases to the patient but at a sufficiently high temperature to be comfortable and effective when supplied to a patient at the end of the conduit.

Humidifiers are often used in a home care environment for use such as the treatment of breathing and sleep apnea disorders and/or with ventilators.

In the home care environment the range of ambient and gas temperatures may well exceed that of the hospital environment. In the home care environment temperatures as low as 10° C. may be present overnight and temperatures over 20° C. may exist during the day. These temperature variations cause the commonly employed control techniques described above to suffer disadvantages.

With the types of humidifiers described, condensation (or rain out) in the breathing conduit will exist, to some degree or other. The degree of condensation is strongly dependent on the ambient temperature, being much greater for greater differences between the ambient temperature and the gas temperature. The formation of large quantities of water in the breathing tubing causes considerable inconvenience to the patient, may accelerate cooling of the gas, may eventually occlude the tubing, or may be expelled into the patient. Also, the patient may experience discomfort when breathing gases which are delivered at temperatures widely divergent from that of the ambient temperature. Excessive condensation also results in inefficient usage of the water in the humidifying chamber of the humidifier.

BRIEF SUMMARY OF THE INVENTION

The present invention improves the control of the temperature of humidified gases supplied by a humidifier having a heating element which heats water in a humidifying chamber to humidify gases supplied to the chamber. The humidifier has electronic control circuitry responsive to an ambient temperature sensor which senses the ambient temperature of the surrounding atmosphere. The humidifier also has a difference temperature selector for selecting a difference temperature, which is the difference in temperature between the temperature at which the humidified gases leave the humidifier chamber and the sensed ambient temperature. Therefore, condensation which usually occurs in the supply conduit at low ambient temperatures is minimised and the patient will experience less discomfort since the humidified gases are delivered at temperatures which carry the maximum water vapour without condensation. This also has the advantage of using the water in the humidifying chamber more efficiently so that the chamber is not required to be refilled as frequently.

BRIEF DESCRIPTION OF THE DRAWINGS

One preferred form of the present invention will now be described with reference to the accompanying drawings in which.

DETAILED DESCRIPTION OF THE PREFERRED EMBODIMENT

Figure 1:
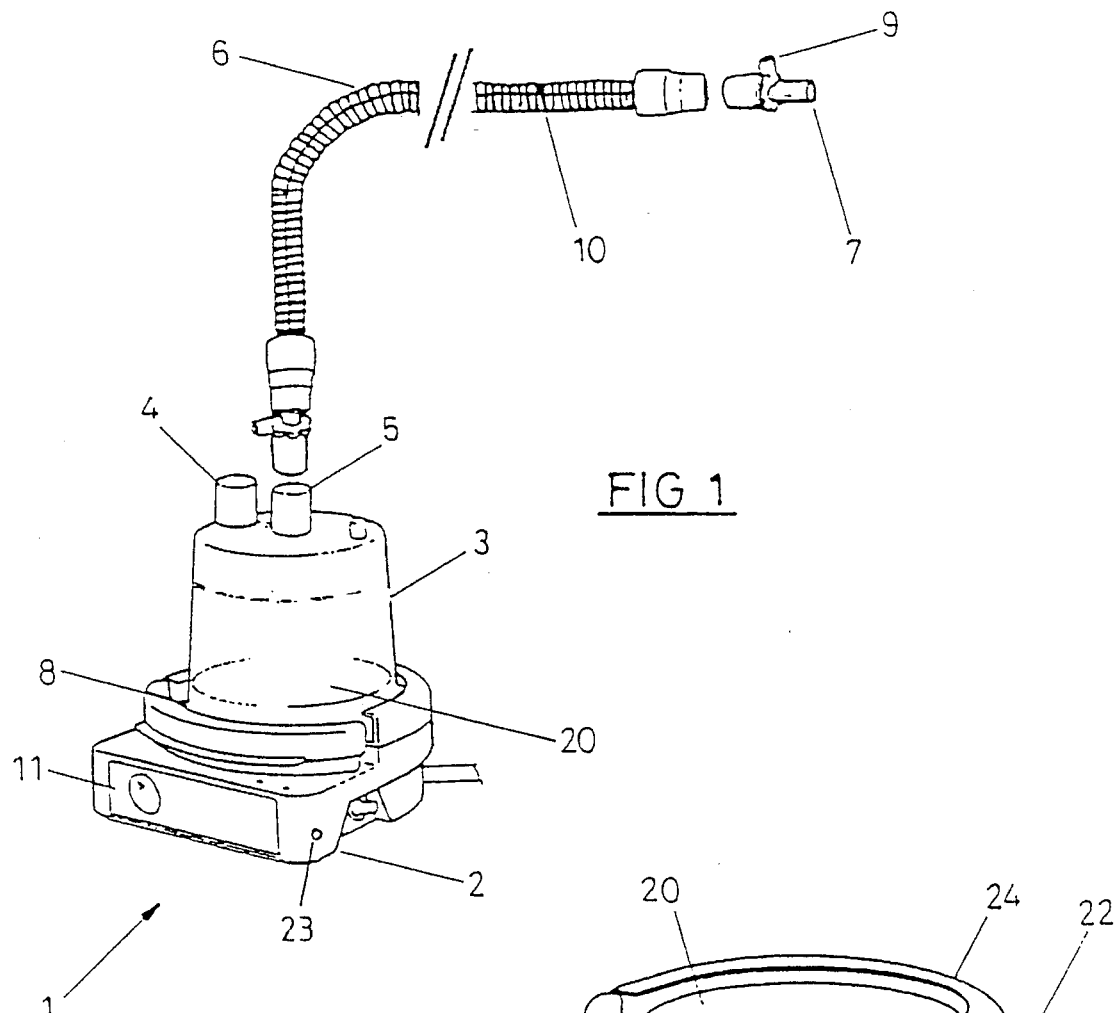
FIG. 1 is a perspective view of humidifying apparatus in accordance with the present invention.
Figure 2:
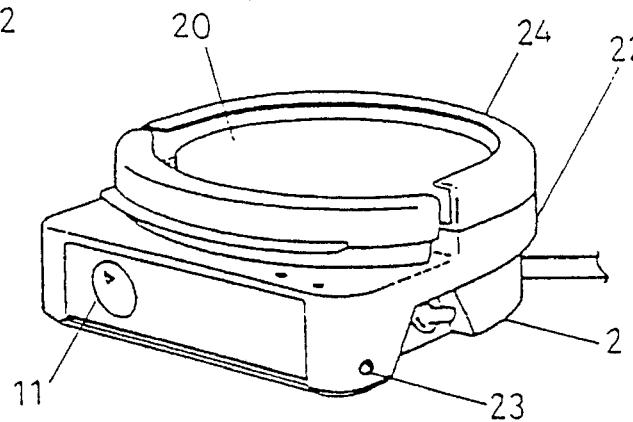
FIG. 2 is a perspective view of humidifying apparatus in accordance with the present invention.
Figure 3:
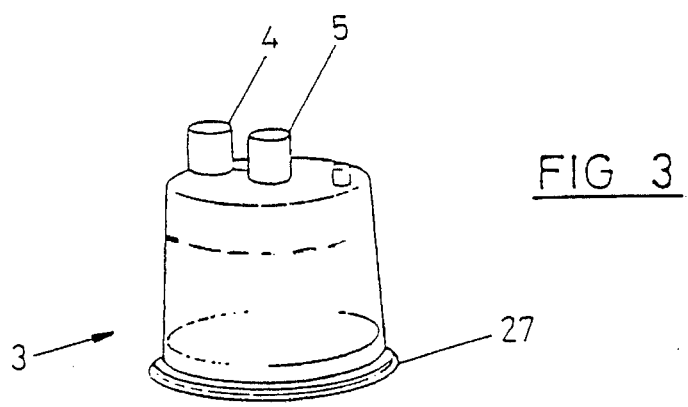
FIG. 3 is a perspective view of a humidifying chamber (not to scale) for use with the apparatus of FIG. 2.

Referring to FIG. 1 a humidifying apparatus generally referenced 1 is shown. The apparatus comprises a body 2 containing heating means comprising a heating plate 20 having an electric heating element therein or in thermal contact therewith and control means, for example, electronic circuitry which may include a microprocessor for controlling the supply of energy to the heating element. The body 2 is removably engageable with a humidifying chamber 3 which contains water for humidifying gases. Referring to FIGS. 2 and 3, which show the humidifier apparatus and the humidifying chamber in more detail, the humidifying chamber 3 has edges 27 which engage with collar 24 on the humidifier apparatus. The gases to be humidified may be a mixture of air, oxygen and anaesthetic, for example, which are supplied to the chamber through a gases inlet 4. A gases outlet 5 is also provided and the gases outlet 5 is connected to the conduit 6 (FIG. 1) which conveys humidified gases to a remote destination such as an intubated patient at the end 7 of the conduit. Alternatively, the end 7 of the conduit may have a gas or face mask attached thereto which mask is used to cover a nose and/or mouth of a user so as to supply humidified gases to the user for breathing. The humidifier heater plate 20 has a temperature transducer 8 which is in electrical connection with the electronic control circuitry in body 2 of the apparatus so that the control means monitors the temperature of the heating plate and the approximate temperature of the humidified gases at the gases outlet 5. Similarly, a further temperature transducer 9 may also be provided at the end 7 of the conduit and this temperature transducer is also in connection with the control circuitry for monitoring the temperature of the humidified gases at the end of the conduit where the humidified gases are supplied to a user. A heating element 10 may also be provided within the conduit 6 to help prevent condensation of the humidified gases within the conduit due to the temperature of the walls of the conduit being close to the ambient temperature, (being the temperature of the surrounding atmosphere) which is usually lower than the temperature of the humidified gases within the conduit.

The present invention overcomes or at least assists in overcoming the problem of condensation in the tubing connecting the humidifier to the patient by controlling the temperature of the heating element 32 in heating plate 20 (FIG. 2), and thus the temperature of the water in the humidifying chamber 3, to a fixed difference temperature above the ambient temperature of the surrounding atmosphere. This is done by providing a selector 11 on the panel of the humidifier, the selector 11 being capable of being adjusted by a user to a selected difference temperature. The difference temperature selected by the user using the selector 11 is the difference temperature between a desired temperature for supply of humidified gases and the ambient temperature. The selector may thus be used to control the temperature of the heater plate or the humidified gases sensed by transducers 8 or 9 to a desired controlled temperature. The control circuitry (FIGS. 4 and 5) controls the temperature of the heating elements to regulate the temperature of the humidified gases leaving the conduit at transducer 9 by controlling the heating element 32 (and therefore heater plate 20) and the conduit heating element 10, so that the temperature of the humidified gases supplied at end 7 of the conduit is governed by a fixed differential temperature to the ambient temperature.

In an alternative embodiment the conduit heating element 10 and the temperature sensor 9 are not provided, and the user must set the differential temperature to ensure that there is minimal condensation occurring in the conduit 6 in use without the temperature or humidity of the humidified gases supplied being too high or low for the gases to be comfortably breathed by a user. The selector 11 may be capable of being adjusted to control heater plate temperature by 5°–55° C., for example, above the sensed ambient temperature. A temperature transducer 45 for measuring the ambient temperature is provided in the humidifier apparatus 2 and supplies signals indicative of the ambient temperature to the control circuitry. It has been observed from our research that the positioning of the ambient temperature transducer should be carefully considered, since the ambient temperature transducer is to indicate ambient temperature. The transducer should be located in a position such that heat generated by the humidifying apparatus does not affect the transducer's measurement.

The ambient temperature sensor may alternatively be constructed in the form of a separate plug-in assembly so that when the plug is connected, the humidifier and the control means act as described above. The plug may be provided at socket 23 (FIG. 2) for example. When the plug is disconnected, the humidifier acts in a conventional manner controlling the heater plate to a temperature determined by the temperature selector 11 without reference to the ambient temperature. From the foregoing it will be seen that a humidifier is provided which controls the temperature of the humidified gases produced by the humidifier to a set differential temperature above the sensed ambient temperature of the surrounding atmosphere. In other words, the temperature of the humidified gases at the gases outlet 5 tracks the the ambient temperature (while maintaining a selected temperature difference from the ambient temperature) so that a decrease in ambient temperature would see the heater plate temperature reduce, further causing the temperature of the humidified gases at the gases outlet 5 to reduce. Thus, when the ambient temperature is expected to vary, for example in a home care environment, the condensation which will occur at low ambient temperatures in the conduit connecting the humidifier to the patient is minimised and the patient will experience less discomfort since the humidified gases are delivered at temperatures which carry the maximum water vapour without condensation. This also has the advantage of using the water in the humidifying chamber more efficiently so that the chamber is not required to be refilled as frequently. Therefore the chamber may not require refilling for a sufficiently long period of time, for example 8 hours.

Figure 4:
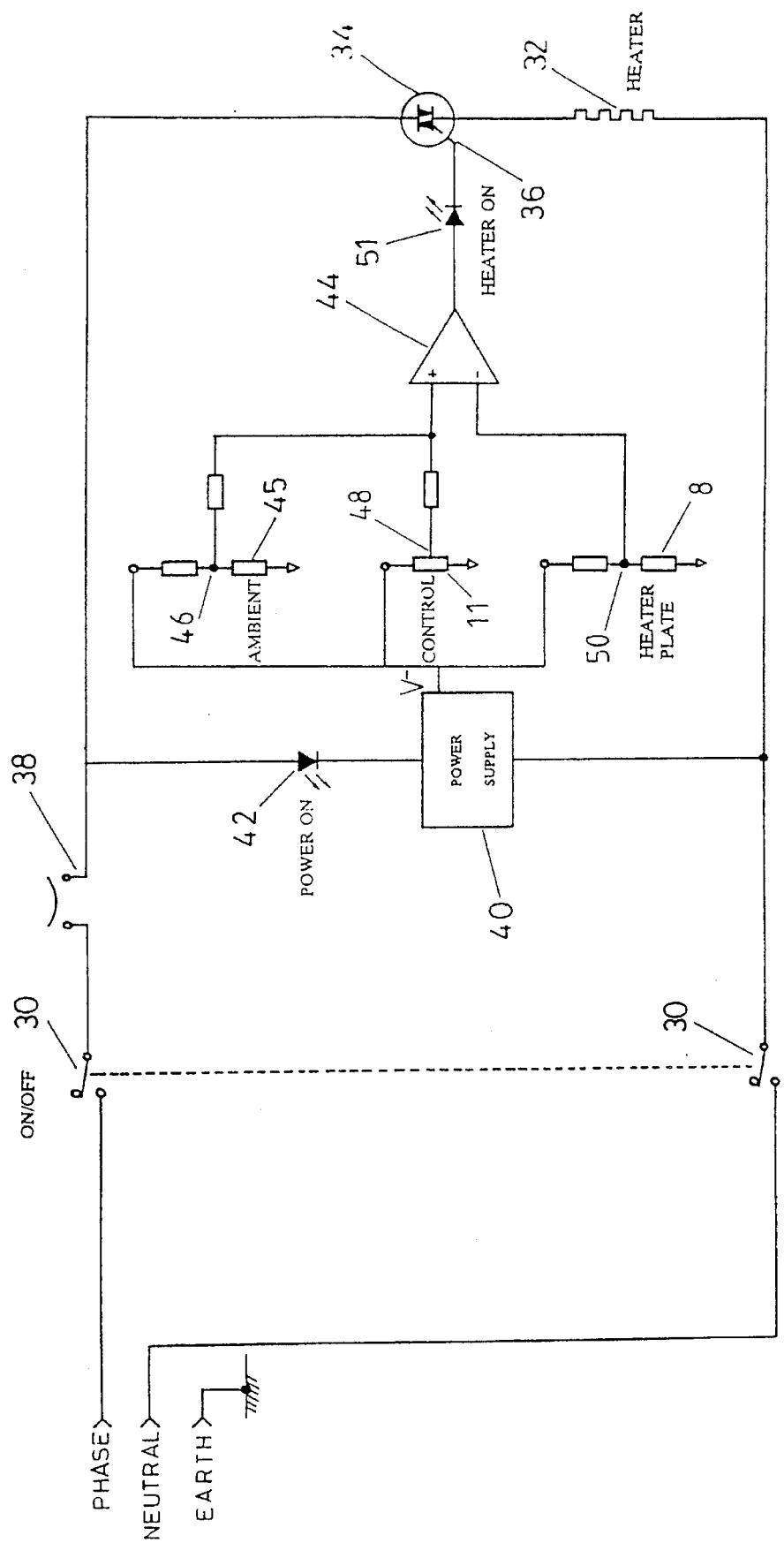
FIG. 4 is a simplified circuit diagram of control circuitry for the humidifying apparatus of the preceding figures.

Referring to FIG. 4 the basic control circuit for the present invention is supplied by an alternating current power supply, for example, a conventional 115 to 230 V 50 or 60 Hz AC mains power supply. The control circuitry is connected to the phase and neutral contacts of the power supply and has a ganged on/off switch 20. The on/off switch 30 connects the power supply to a heating element 32 provided in the heater plate 20. The heating element is for example an 85 Watt heating element, but elements of other desired heating capacities may be provided. The heating element is connected with the supply by a TRIAC 34 having a gate electrode 36. As a safety precaution, a temperature dependent circuit breaker 38 is provided which is normally closed, but which will open when the heater plate 30 exceeds a predetermined temperature, for example 93° C. When such a temperature is reached, the contacts of the circuit breaker 38 will open and prevent any further power being supplied to the heating element to prevent overheating of the apparatus, which may result in either damage to the apparatus or injury to the patient. The mains power supply provides power to a further power supply 40 which is a low voltage DC power supply (for example 10 to 15 volts) for supplying power to the electronic circuitry.

An amplifier such as an operational amplifier 44 is provided as part of the electronic circuitry and the power supply for the operational amplifier 44 is provided by supply 40. The power supply 40 also supplies power to the resistor networks in which the variable resistance temperature sensors 8 and 45 are provided. The supply 40 supplies power to the ambient temperature transducer 45 at point 46, the variable resistance difference temperature selector 11 at point 48, and the heater plate temperature transducer 8 at point 50 in the circuit. The ambient temperature transducer 45 and difference temperature selector output are provided to the non-inverting input of the operational amplifier 44. The inverting input of operational amplifier 44 is connected to the output of the heater plate temperature transducer 8. Thus the signals provided by the difference temperature selector 11 and the ambient temperature transducer 45 are added on the non-inverting side of the operational amplifier, and when the added signal on the non-inverting side of the operational amplifier is greater than the signal supplied to the non-inverting input from the heater plate transducer 8, then the operational amplifier will supply a signal to the gate 36 of the TRIAC 34 to switch the heating element 32 on. When the output of the operational amplifier 44 supplies the "on" signal to the gate 36, an LED 51 is switched on to indicate that the heating element 32 is in the "on" state.

Figure 5:
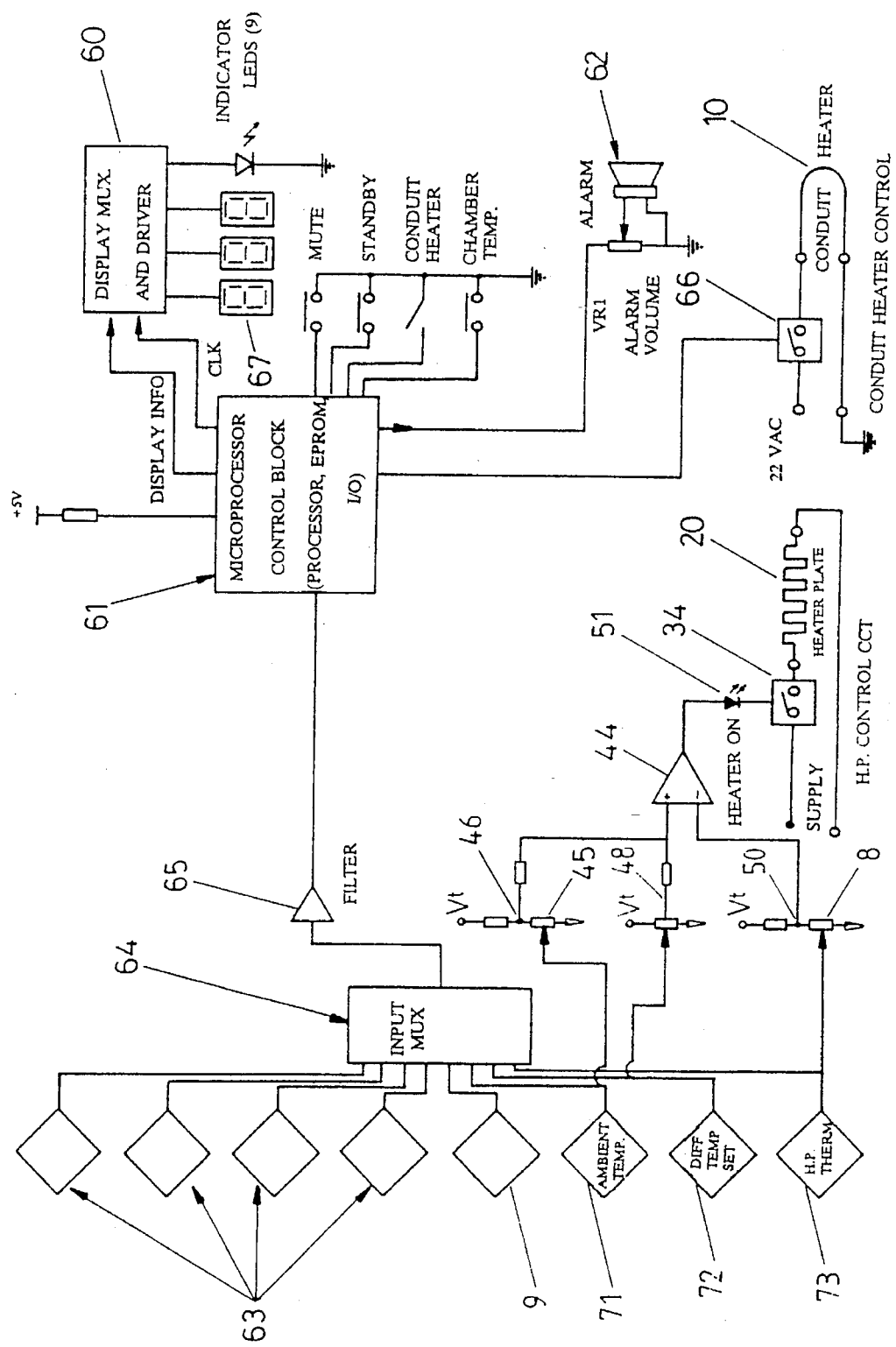
FIG. 5 is a simplified block diagram of control circuitry for the humidifying apparatus of the present invention.

FIG. 5 demonstrates a simplified block diagram of an embodiment of the control circuitry incorporating the previously described heater plate controller. An input multiplexer 64 is supplied with a series of inputs including ambient temperature 71, difference temperature 72 and heater plate temperature 73 which control the heating of the heater plate as previously described. A number of other variables may be sensed including the temperature of the humidified gases at end 10 of the conduit by transducer 9.

Other possible inputs are provided being referenced 63. The various inputs are multiplexed, then electrically filtered by filter 65 before being provided to a microprocessor controller 61. The microprocessor 61 executes steps in a software program which enable it to display information (for example ambient temperature or difference temperature) on a display 67 which is controlled by a display multiplexer and driver 60. The microprocessor 61 also operates an audio alarm 62 upon sensing undesirable circumstances or faults. The conduit heater 10 may also be switched on or off upon instructions by the microprocessor 61. The switch 66 may be a TRIAC controlled by the microprocessor in a similar way to switch 34 in the heater state control circuit. It can be seen that the heater plate controls as previously herein described could also be incorporated in the software program of the microprocessor.

The present invention provides a humidifier and controls for a humidifier which allow humidified gases to be supplied to a patient at a fixed temperature above the ambient temperature of the surrounding atmosphere.

We claim:

1. A respiratory humidifier comprising:

a humidifying chamber having a gases outlet;

a delivery conduit extending between said gases outlet of said humidifying chamber and a user, said delivery conduit being exposed to ambient temperature;

heating means energizable to heat water in said humidifying chamber to humidify gases supplied to said humidifying chamber;

control means which, on occasion, energize said heating means;

ambient temperature sensing means to sense the ambient temperature of the surrounding atmosphere; and differential temperature selection means to allow a user to select a value representative of a desired temperature difference between the temperature of humidified gases supplied by the humidifier chamber and ambient temperature;

said ambient temperature sensing means and said differential temperature selection means respectively providing an indication of the ambient temperature and said value representative of a desired difference temperature to said control means;

said control means calculating a desired gases outlet temperature as the sum of the sensed ambient temperature and said value representative of a desired difference temperature such that said gases outlet temperature tracks said ambient temperature;

said control means selectively energizing said heating means to control the temperature of said humidified gases supplied by said humidifier at said gases outlet to said calculated temperature to thereby minimize condensation of said humidified gases passing through said delivery conduit.

2. A respiratory humidifier as claimed in claim 1 wherein said control means includes algebraic adding means for algebraically adding said value representative of said difference temperature to said ambient temperature to provide said controlled temperature.

3. A respiratory humidifier as claimed in claim 1 wherein said control means controls said heating means dependent on the temperature sensed by said ambient temperature sensing means and the value representative of the temperature selected by said difference temperature selection means to supply heat to said humidifying chamber to provide said humidified gases at said controlled temperature.

4. A respiratory humidifier as claimed in claim 1 wherein a temperature sensing means is provided for sensing the temperature of the humidified gases supplied by said humidifier, said temperature sensing means providing an indication of the temperature of said humidified gases to said control means.

5. A respiratory humidifier as claimed in claim 1 wherein said control means includes algebraic adding means for algebraically adding said value representative of said difference temperature to said ambient temperature to provide said controlled temperature.

6. A respiratory humidifier as claimed in claim 1 wherein said control means controls said heating means dependent on the temperature sensed by said ambient temperature sensing means and the value representative of temperature selected by said difference temperature selection means to supply heat to said humidifying chamber to provide said humidified gases at said controlled temperature.

7. A respiratory humidifier as claimed in claim 1 wherein a temperature sensing means is provided for sensing the temperature of the humidified gases supplied by said humidifier, said temperature sensing means providing an indication of the temperature of said humidified gases to said control means.

* * * * *